United States Patent
Schunk et al.

(10) Patent No.: US 6,976,281 B2
(45) Date of Patent: Dec. 20, 2005

(54) MEDICINAL CUSHION, IN PARTICULAR ANTI-DECUBITUS CUSHION

(75) Inventors: Werner Schunk, Gotha (DE); Michael Bruder, Hamburg (DE); Karl-Heinz Krause, Chemnitz (DE); Gerhard Merkmann, Gotha (DE); Jörg Vortkort, Wulfsen (DE)

(73) Assignee: INTECH Thüringen GmbH, Waltershausen (DE)

( * ) Notice: Subject to any disclaimer, the term of this patent is extended or adjusted under 35 U.S.C. 154(b) by 0 days.

(21) Appl. No.: 10/415,856

(22) PCT Filed: Aug. 8, 2002

(86) PCT No.: PCT/DE02/02916

§ 371 (c)(1),
(2), (4) Date: Sep. 3, 2003

(87) PCT Pub. No.: WO03/026708

PCT Pub. Date: Apr. 3, 2003

(65) Prior Publication Data

US 2004/0049854 A1    Mar. 18, 2004

(30) Foreign Application Priority Data

Sep. 3, 2001    (DE) ................................ 101 42 876

(51) Int. Cl.[7] .............................................. A61L 15/44

(52) U.S. Cl. ............................................. 5/710; 5/654

(58) Field of Search ........................... 5/710, 713, 654, 5/120, 122, 127, 129

(56) References Cited

U.S. PATENT DOCUMENTS

| | | | |
|---|---|---|---|
| 531,727 A * | 1/1895 | Keegan, Sr. et al. ............. | 5/129 |
| 679,963 A * | 8/1901 | Hayward ........................ | 5/129 |
| 944,784 A * | 12/1909 | Hand ............................. | 5/129 |
| 4,347,633 A * | 9/1982 | Gammons et al. ............. | 5/713 |
| 4,541,136 A | 9/1985 | Graebe | |
| 4,698,864 A | 10/1987 | Graebe | |
| 5,052,068 A | 10/1991 | Graebe | |
| 5,255,404 A * | 10/1993 | Dinsmoor, III et al. ......... | 5/677 |
| 5,475,882 A * | 12/1995 | Sereboff ..................... | 5/655.4 |
| 6,415,467 B1 * | 7/2002 | Bretvin .......................... | 5/710 |
| 6,519,797 B1 * | 2/2003 | Brubaker et al. ............... | 5/654 |
| 6,660,901 B2 * | 12/2003 | Church ........................ | 602/48 |
| 6,748,616 B1 * | 6/2004 | Tseng ............................ | 5/710 |

FOREIGN PATENT DOCUMENTS

| | | |
|---|---|---|
| DE | 278 492 | 5/1990 |
| DE | 278 494 | 5/1990 |
| DE | 297 13 160 | 3/1998 |
| DE | 198 12 772 | 9/1999 |
| GB | 2326827 A * | 1/1999 |
| WO | WO 89/05661 | 6/1989 |
| WO | WO 92/07492 | 5/1992 |
| WO | WO 94/10881 | 5/1994 |

(Continued)

Primary Examiner—Michael Trettel
(74) Attorney, Agent, or Firm—Collard & Roe, P.C.

(57) ABSTRACT

A medical cushion (1), in particular an anti-decubitus cushion, is in particular multicellular and is distinguished in that the cushion is equipped, at least in the area where skin contact (6) occurs, with an active membrane (3) based on a skin-compatible matrix (4) into which a molecular sieve is mixed. This molecular sieve is charged with at least one active substance ($Z$, $Z_1$, $Z_2$), and the molecular sieve/active substance adduct (5) releases the active substance when the active membrane comes into skin contact (6) in conjunction with the transpiration of the skin.

32 Claims, 2 Drawing Sheets

FOREIGN PATENT DOCUMENTS

| WO | WO 96/12426 | 5/1996 |
| WO | WO 01/70202 | 9/2001 |
| WO | WO 02/30196 | 4/2002 |
| WO | WO 02/30388 | 4/2002 |
| WO | WO 02/43844 | 6/2002 |

* cited by examiner

# MEDICINAL CUSHION, IN PARTICULAR ANTI-DECUBITUS CUSHION

CROSS REFERENCE TO RELATED APPLICATIONS

Applicants claim priority under 35 U.S.C. §119 of German Application No. 101 42 876.6, filed Sep. 3, 2001. Applicants also claim priority under 35 U.S.C. §365 of PCT/DE02/02916, filed Aug. 8, 2002. The international application under PCT article 21(2) was not published in English.

The invention relates to a medical cushion, in particular an anti-decubitus cushion, which is in particular multicellular.

Wounds or pressure sores are presently prevented and healed using, among other things, skins, foam supports (DE 297 13 160 U1), gel cushions, or cushions filled with plastic balls. The most effective, however, have proven to be multicellular inflatable cushions. These are described, for example, in patent specifications U.S. Pat. Nos. 4,541,136 and 5,052,068. These cushions are produced in an immersion process using synthetic rubbers. The preferred geometry of the cells is described in detail in patent specification U.S. Pat. No. 4,698,864. The preferred material named in said patent specification is neoprene. The presently known inflatable cushions have one or more inflatable areas. Systems for air exchange between the individual cells and for inflating the individual areas are described in laid-open specifications WO 92/07492 A1 and WO 94/10881 A1. The air exchange between the cells takes place via valves located on the underside of the cushion. The individual areas are inflated via tubes and valve systems which, in order to permit better operation, are preferably arranged together at one location on the cushion. The height and surface area of the individual cells can be varied across the surface of the cushion. By means of the particular geometry of the cells, the cushion can be adapted to the body shape and body weight.

Laid-open specification WO 96/12426 A1 also describes an inflatable cushion which can be produced in a vacuum process or thermoforming process. For this cushion, thermoplastics are used which can be processed by the aforementioned methods. These cushions are preferably produced from polyethylene, polypropylene, polyester, nylon, polyvinyl chloride, polyvinylidene and polyurethane. The underside of the thermoformed cushion is sealed with a foil, for example by welding or adhesive bonding. This cushion likewise consists of one or more areas which are inflated with air. The system for air exchange, consisting of valves and tubes, is located on the underside of the cushion. The geometry of the cells can vary in height and area.

As regards the prior art relevant in this connection, reference is also made to German laid-open specification DE 198 12 772 A1.

The following factors are of importance in the development of ulcers (decubitus ulcers), namely pressure on the tissue, a moist micro-environment near the skin, and infectious microorganisms. To prevent decubitus ulcers, the following basic functional properties must therefore be taken into account:

micro-climate properties by regulating the water content or by buffering the increase in moisture in the micro-environment near the skin;

reducing pressure by means of the compressive elastic behavior of the cushion;

avoiding or reducing the number of multiresistant microorganisms, with particular importance being given to treatment with an antibiotic.

In the context of a further development, the object of the invention is now to design a medical cushion, in particular an anti-decubitus cushion, in such a way that, on the one hand, the abovementioned criteria are taken into account and, on the other hand, the range of medical treatments is broadened.

As is set forth in patent claim 1, this object is achieved by the fact that the cushion is equipped, at least in the area where skin contact occurs, with an active membrane based on a skin-compatible matrix into which a molecular sieve is mixed, said molecular sieve being charged with at least one active substance, and the molecular sieve/active substance adduct releasing the active substance when the active membrane comes into skin contact in conjunction with the transpiration of the skin.

According to a particularly advantageous embodiment of the invention, the medical cushion as claimed in claim 2 is distinguished in that the molecular sieve/active substance adduct additionally contains crystallization water, specifically such that the molecular sieve is partially dehydrated in relation to a sufficient base mol quantity (m) of crystallization water, and said molecular sieve containing the reduced mol quantity (m') of crystallization water is charged with the active substance such that, when the active membrane comes into skin contact, adsorption of water takes place during desorption of the active substance and the crystallization water content of the molecular sieve increases.

Further expedient alternative embodiments of the medical cushion are set forth in patent claims 3 through 20.

The object of the invention is additionally to make available a method for producing a medical cushion of this kind.

This additional object is achieved by the following method steps:

the molecular sieve is charged with at least one active substance to form the molecular sieve/active substance adduct;

the molecular sieve/active substance adduct is then mixed into the matrix to form the active membrane;

finally, the active membrane is assembled with the medical cushion.

The charging is carried out in particular at normal pressure in the presence of an inert gas, for example nitrogen, and specifically using a mortar mill or ball mill.

In connection with the partial dehydration, the following method steps are expediently used:

the molecular sieve with a sufficient base mol quantity (m) of crystallization water is partially dehydrated at 100 to 500° C., preferably at 350 to 450° C., for several hours, preferably for 2 to 6 hours;

the partially dehydrated molecular sieve with the reduced mol quantity (m') of crystallization water is then charged with at least one active substance to form the molecular sieve/active substance adduct.

The dehydration is also carried out here in particular at normal pressure in the presence of an inert gas.

The invention is now explained on the basis of illustrative embodiments and with reference to diagrammatic drawings, in which.

Figure 1:
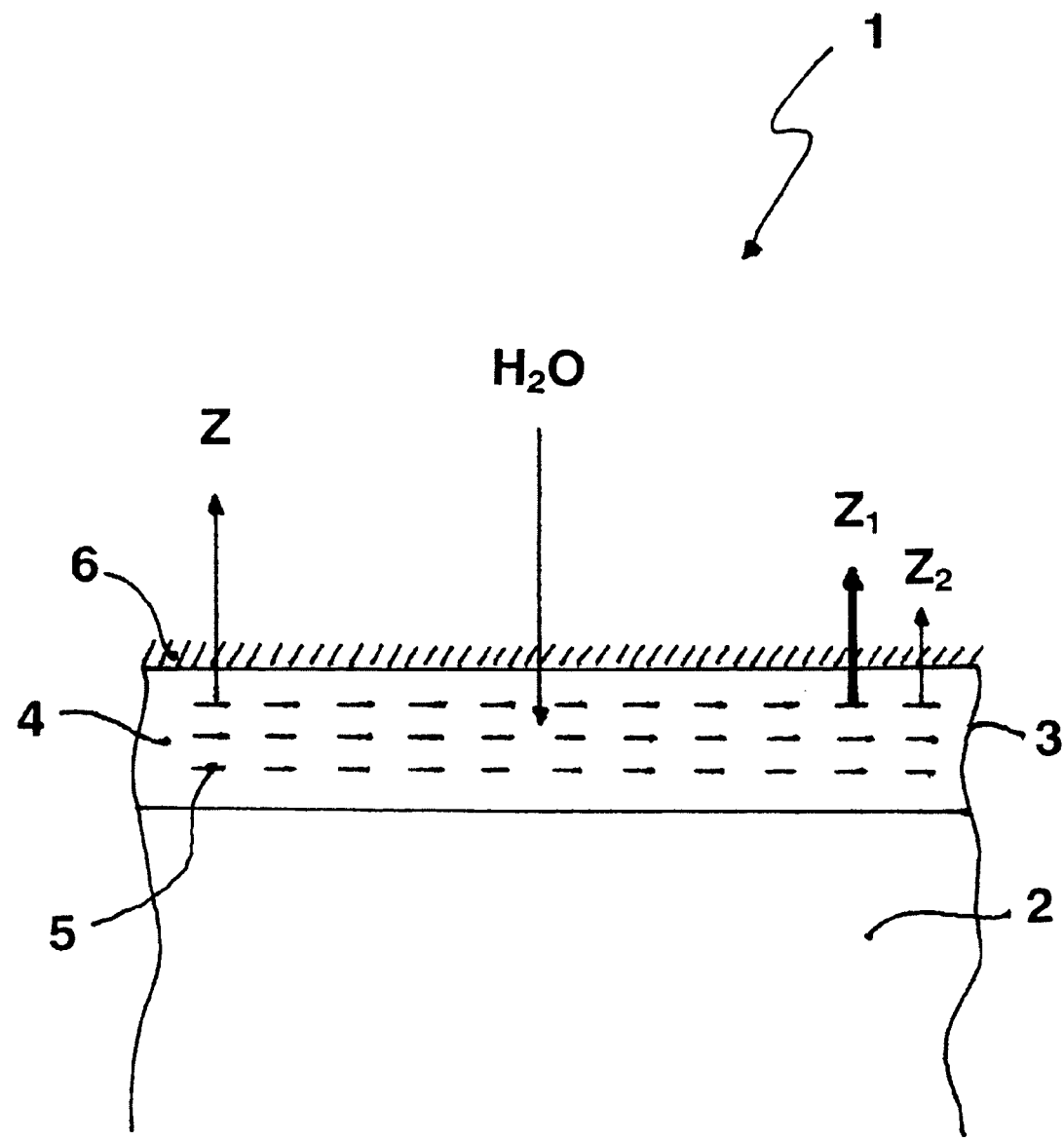
FIG. 1 shows the adsorption/desorption mechanism on the basis of two illustrative embodiments.

In the form of a composite body, the anti-decubitus cushion 1 according to FIG. 1, intended principally for hospital use, comprises a cellular main body 2 and an active membrane 3. Dome cushions, foam cushions and geotextile cushions can be used, for example, as the main body. The multicellular inflatable cushions are of particular importance here. Regarding details of construction and materials, reference is made to the prior art cited at the outset.

The active membrane 3 in turn consists of the matrix 4 into which the molecular sieve/active substance adduct 5 is mixed. The molecular sieve used is in particular a sodium aluminum silicate of the formula

$$Na_{86}[(AlO_2)_{86} \cdot (SiO_2)_{106}] \cdot m(m')H_2O$$

which, in the state when not yet dehydrated, contains a base mol quantity (m=276) of crystallization water. In the context of the partial dehydration, at least 20%, preferably 40 to 70%, mol of water are removed. The partially dehydrated molecular sieve containing the reduced mol quantity (m'; e.g. m'=200) is then charged with an active substance Z.

When the active membrane 3 makes skin contact 6, water is removed from the skin or the wound area and is taken up by the molecular sieve/active substance adduct 5 (adsorption), with desorption of the active substance Z taking place. In this process, the crystallization water content of the molecular sieve increases. The molecular sieve thus recovers the crystallization water which has been removed in the context of the partial dehydration.

The fact that the molecular sieve/active substance adduct 5 contains crystallization water ensures an appropriate moist environment. This facilitates the desorption of the active substance Z by means of the solvent and dispersant (water). In addition, the moist environment creates ideal conditions for cell growth factors and also helps the immune defense.

Examples of active membranes are:
active membrane with antibiotic (against bacterial infections)
active membrane with prednisolone (against inflammation)
active membrane with vitamin A acid (against keratinization)
active membrane with antithrombotic (against thrombosis)

Another illustrative embodiment is represented in the same figure. Here, with a uniform degree of dehydration, the molecular sieve is charged with a first active substance $Z_1$ and a second active substance $Z_2$ which are distinguished by a different degree of charging so that, when the active membrane 3 makes skin contact 6, the molecular sieve/active substance adduct 5 releases the active substances $Z_1$ and $Z_2$ sequentially, as is indicated by the different arrow thicknesses. The two active substances here have approximately the same molecular weight. The following numerical example is intended to illustrate this. The molecular sieve has a degree of dehydration of 70%. With a total degree of charging of active substances $Z_1$ and $Z_2$ of 60%, $Z_1$ accounts for 40% and $Z_2$ for 20%. On account of its larger charge, active substance $Z_1$ is released more rapidly than active substance $Z_2$, in connection with a time-delay therapeutic effect.

Figure 2:
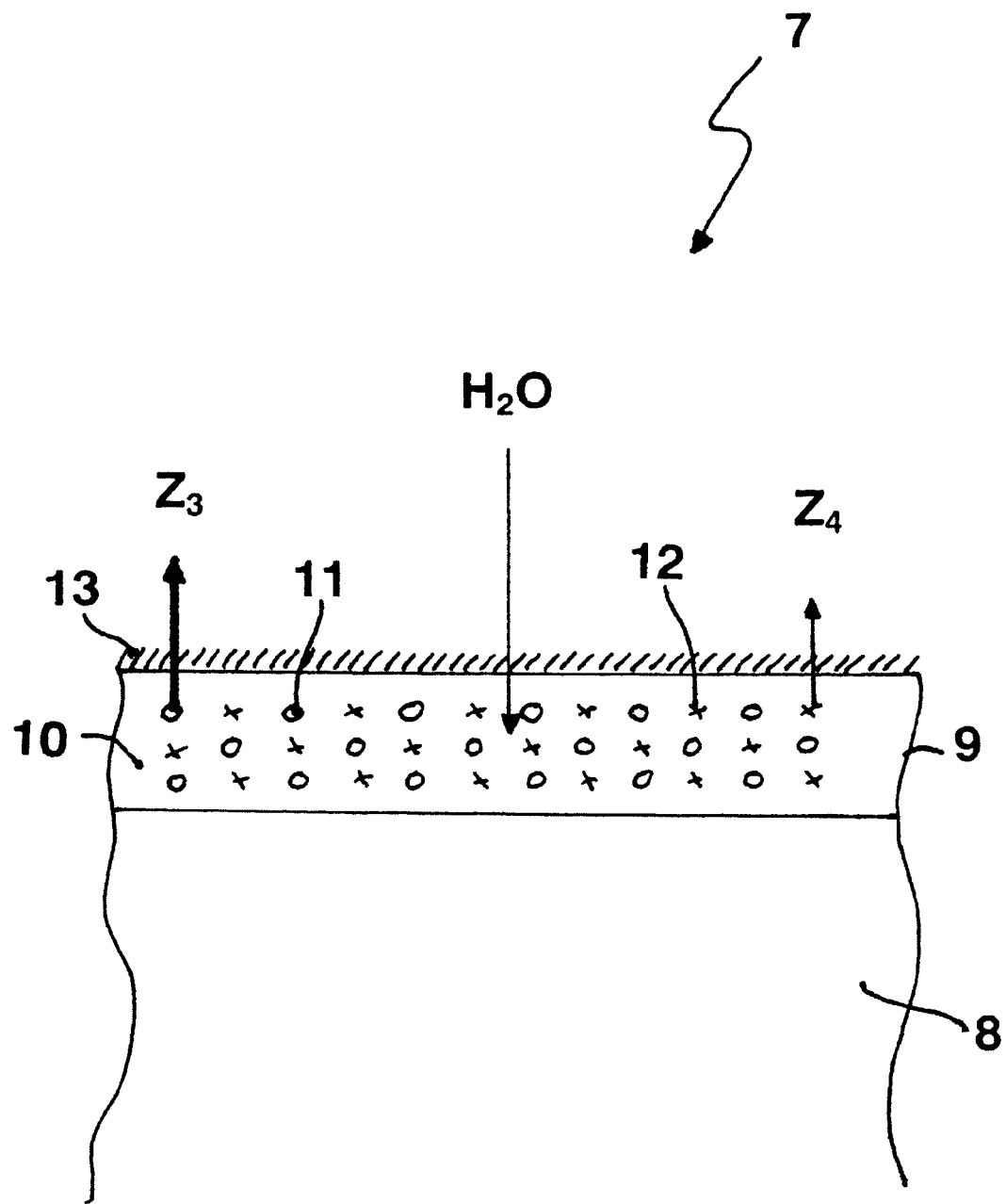
FIG. 2 shows the adsorption/desorption mechanism on the basis of two molecular sieve/active substance adducts which have a different degree of dehydration.

One example of a medical application in this sense would be the combination of an antithrombotic ($Z_1$) and an antibiotic ($Z_2$), and this can also apply to the illustrative example in FIG. 2, which will now be explained in detail.

A first molecular sieve 11 and a second molecular sieve 12 are mixed into the matrix 10, these molecular sieves 11 and 12 being of the same type, but being distinguished by a different degree of dehydration, as in the following example:

molecular sieve type: $Na_{86}[(AlO_2)_{86} \cdot (SiO_2)_{106}] \cdot m(m')H_2O$
base mol quantity (m) before partial dehydration: m=276
reduced mol quantity (m')
molecular sieve/active substance adduct 11 with active substance $Z_3$: m'=100
molecular sieve/active substance adduct 12 with active substance $Z_4$: m'=200

With approximately the same molecular weight of the active substances $Z_3$ and $Z_4$, the degree of charging of each is approximately identical.

When the active membrane 9 makes skin contact 13, the active substances $Z_3$ and $Z_4$ are released sequentially, as is once again symbolized by the different arrow thicknesses. In other words, the adduct 11 with the greater degree of dehydration will take up water more quickly than the adduct 12. The consequence of this is that the active substance $Z_3$ is released more rapidly than the active substance $Z_4$, again in connection with a time-delay therapy effect.

Independently of the illustrative embodiments, the following parameters expediently apply for active membranes 1 and 7:

The adducts 5, 11 and 12 are distributed substantially uniformly within the matrix 4 and 10.

The adducts 5, 11 and 12 have a proportion of 2 to 20% by weight, preferably 5 to 10% by weight, specifically relative to the total mass of the active membrane 3 and 9.

The matrix 4 and 10 is a polymer, in particular an elastomer, a thermoplastic elastomer or a thermoplastic. It is important in this connection that these materials form a skin-compatible matrix.

The active membrane 3 and 9 has a layer thickness of 0.5 mm to 2 mm, preferably 1 mm.

The active membrane 3 and 9 can be covered with a tear-off protective foil, which is removed before use.

The statements contained in the description and in the patent claims concerning the degree of dehydration and the degree of charging relate to the state after completion of the partial dehydration or charging, i.e. without metabolic exchange of water and active substance.

In combining the known medical cushions with the novel active membrane, it has become possible to substantially improve prevention of decubitus ulcers. In addition, other conditions can be treated at the same time.

| List of reference numbers | |
|---|---|
| 1 | medical cushion (anti-decubitus cushion) |
| 2 | cellular main body |
| 3 | active membrane |
| 4 | matrix |
| 5 | molecular sieve/active substance adduct with active substances Z, $Z_1$, $Z_2$ |
| 6 | skin contact |
| 7 | medical cushion (anti-decubitus cushion) |
| 8 | cellular main body |
| 9 | active membrane |
| 10 | matrix |
| 11 | molecular sieve/active substance adduct with active substance $Z_3$ |
| 12 | molecular sieve/active substance adduct with active substance $Z_4$ |
| 13 | skin contact |

What is claimed is:

1. A medical cushion (1, 7), which is a multicellular anti-decubitus cushion, comprising
   a cushion which is equipped, where skin contact (6, 13) occurs, with an active membrane (8, 9) based on a skin-compatible matrix (4, 10) into which a molecular sieve is mixed,
   said molecular sieve being charged with at least one active substance (Z, $Z_1$, $Z_2$, $Z_3$, $Z_4$), and a molecular sieve/active substance adduct (5, 11, 12) releases the active substance when the active membrane comes into skin contact (6, 13) in conjunction with the transpiration of the skin, and
   wherein the molecular sieve/active substance adduct (5, 11, 12) additionally contains crystallization water, such that the molecular sieve is partially dehydrated in relation to a sufficient base mol quantity (m) of crystallization water, and
   said molecular sieve containing the reduced mol quantity (m') of crystallization water is charged with the active substance (Z, $Z_1$, $Z_2$, $Z_3$, $Z_4$) such that, when the active membrane (3, 9) comes into skin contact (6, 13), adsorption of water takes place during desoroption of the active substance and the crystallization water content of the molecular sieve increases.

2. The medical cushion as claimed in claim 1, wherein the molecular sieve is a metal aluminum silicate of the following formula:
   $Me_n[(AlO_2)_x \cdot (SiO_2)_Y]$; and a content of crystallization water selected from the group consisting of with crystallization water and without crystallization water.

3. The medical cushion as claimed in claim 1, wherein the molecular sieve is a metal aluminum silicate of the following formula:
   $$Me_n[(AlO_2)_x \cdot (SiO_2)_Y] \cdot m(m') \, H_2O.$$

4. The medical cushion as claimed in claim 2, wherein a metal of the first or second main group of the periodic table is used.

5. The medical cushion as claimed in claim 4, wherein sodium is used as metal.

6. The medical cushion as claimed in claim 2, wherein the molecular sieve is a sodium aluminum silicate of the following formula:
   $Na_{86}[(AlO_2)_{86} \cdot (SiO_2)_{106}]$; and with a content of crystallization water selected from the group consisting of with crystallization water and without crystallization water.

7. The medical cushion as claimed in claim 3, wherein the molecular sieve is a sodium aluminum silicate of the following formula:
   $$Na_{86}[(AlO_2)_{86} \cdot (SiO_2)_{106}] \cdot m(m') \, H_2O.$$

8. The medical cushion as claimed in claim 1, wherein the molecular sieve contains a base mol quantity (m) of crystallization water of at least 100.

9. The medical cushion as claimed in claim 7, wherein the molecular sieve is a sodium aluminum silicate of the following formula:
   $$Na_{86}[(AlO_2)_{86} \cdot (SiO_2)_{106}] \cdot 276 \, H_2O.$$

10. The medical cushion as claimed in claim 1, wherein the partially dehydrated molecular sieve has a degree of dehydration of at least 20%.

11. The medical cushion as claimed in claim 1, wherein the degree of charging of the active substance (Z, $Z_1$, $Z_2$, $Z_3$, $Z_4$) in the molecular sieve/active substance adduct (5, 11, 12) is smaller than the degree of dehydration of the partially dehydrated molecular sieve.

12. The medical cushion as claimed in claim 11, wherein the degree of charging is at least 50% of the degree of dehydration.

13. The medical cushion as claimed in claim 1, wherein the molecular sieve/active substance adduct (5, 11, 12) is distributed substantially uniformly within the matrix (4, 10) of the active membrane (3, 9).

14. The medical cushion as claimed in claim 1, wherein the molecular sieve/active substance adduct (5, 11, 12) has a proportion of 2 to 20% by weight, specifically relative to the total mass of the active membrane (3, 9).

15. The medical cushion as claimed in claim 1, wherein the matrix (4, 10) of the active membrane (3, 9) is selected from the group consisting of a polymer, an elastomer, a thermoplastic elastomer and a thermoplastic.

16. The medical cushion as claimed in claim 1, wherein the active membrane (3, 9) has a layer thickness of 0.5 mm to 2 mm.

17. The medical cushion as claimed in claim 1, wherein with a uniform degree of dehydration, the molecular sieve is charged with at least a first active substance ($Z_1$) and a second active substance ($Z_2$) which are distinguished by a different degree of charging,
   so that the molecular sieve/active substance adduct (5) releases the active substances ($Z_1$, $Z_2$) sequentially when the active membrane (3) makes skin contact (6).

18. The medical cushion as claimed in claim 1, wherein at least a first molecular sieve and a second molecular sieve are mixed into the matrix (10), which molecular sieves are of the same type but are distinguished by a different degree of dehydration, the first molecular sieve being charged with a first active substance ($Z_3$) and the second molecular sieve being charged with a second active substance ($Z_4$), and specifically with an approximately identical degree of charging,
   so that a first molecular sieve/active substance adduct (11) and a second molecular sieve/active substance adduct (12) release the active substances ($Z_3$, $Z_4$) sequentially when the active membrane (9) makes skin contact (13).

19. The medical cushion as claimed in claim 1, wherein the active membrane (3, 9) is exchangeable.

20. A method for producing a medical cushion (1, 7) comprising the following method steps:
    charging a molecular sieve with at least one active substance (Z, $Z_1$, $Z_2$, $Z_3$, $Z_4$) to form a molecular sieve/active substance adduct (5, 11, 12); and carrying out the charging at normal pressure;
    mixing the molecular sieve/active substance adduct (5, 11, 12) into the matrix (4, 10) to form the active membrane (3, 9); and
    finally, assembling the active membrane (3, 9) with the medical cushion (1, 7).

21. The method as claimed in claim 20, comprising carrying out the charging using a mortar mill or ball mill.

22. The method as claimed in claim 20, comprising carrying out the charging in the presence of an inert gas.

23. The method as claimed in claim 20, comprising the following method steps:
    partially dehydrating the molecular sieve with a sufficient base mol quantity (m) of crystallization water at 100 to 500° C., for several hours;

charging the partially dehydrated molecular sieve with the reduced mol quantity (m') of crystallization water with at least one active substance (Z, $Z_1$, $Z_2$, $Z_3$, $Z_4$) to form the molecular sieve/active substance adduct (5, 11, 12);

mixing the molecular sieve/active substance adduct (5, 11, 12) into the matrix (4, 10) to form the active membrane (3, 9); and finally, assembling the active membrane (3, 9) with the medical cushion (1, 7).

24. The method as claimed in claim 23, comprising carrying out the dehydration at normal pressure.

25. The method as claimed in claim 23, comprising carrying out the dehydration in the presence of an inert gas.

26. The medical cushion as claimed in claim 8, wherein the molecular sieve contains a base mol quantity (m) of crystallization water of at least 200.

27. The medical cushion as claimed in claim 10, wherein the partially dehydrated molecular sieve has a degree of dehydration of 40% to 70%.

28. The medical cushion as claimed in claim 14, wherein the molecular sieve/active substance adduct (5, 11, 12) has a proportion of 5 to 10% by weight, specifically relative to the total mass of the active membrane (3, 9).

29. The medical cushion as claimed in claim 16, wherein the active membrane (3, 9) has a layer of thickness of 1 mm.

30. The method as claimed in claim 22, comprising carrying out the charging in the presence of nitrogen.

31. The method as claimed in claim 23, comprising the following method steps:

partially dehydrating the molecular sieve with a sufficient base mol quantity (m) of crystallization water at 350 to 450° C., for 2 to 6 hours;

charging the partially dehydrated molecular sieve with the reduced mol quantity (m') of crystallization water with at least one active substance (Z, $Z_1$, $Z_2$, $Z_3$, $Z_4$) to form the molecular sieve/active substance adduct (5, 11, 12);

mixing the molecular sieve/active substance adduct (5, 11, 12) into the matrix (4, 10) to form the active membrane (3, 9); and finally assembling the active membrane (3, 9) with the medical cushion (1, 7).

32. The method as claimed in claim 25, comprising carrying out the dehydration in the presence of nitrogen.

* * * * *